(12) United States Patent
Pedersen et al.

(10) Patent No.: US 6,486,188 B1
(45) Date of Patent: Nov. 26, 2002

(54) METHOD OF TREATMENT FOR CARDIOVASCULAR COMPLICATIONS

(75) Inventors: Erling Bjerregaard Pedersen, Holstebro (DK); Friedrich Luft, Schwanebeck-Berlin (DE); Anders Svensson, Mölndal (SE); Faies Zannad, Villers Les Nancy (FR)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/720,289
(22) PCT Filed: Jul. 5, 2000
(86) PCT No.: PCT/SE00/01444
§ 371 (c)(1),
(2), (4) Date: Dec. 22, 2000
(87) PCT Pub. No.: WO01/01987
PCT Pub. Date: Jan. 11, 2001

(30) Foreign Application Priority Data

Jul. 6, 1999 (SE) ................................................ 9902597

(51) Int. Cl.⁷ ............................................. A61K 31/41
(52) U.S. Cl. ...................................................... 514/382
(58) Field of Search .......................................... 514/382

(56) References Cited

FOREIGN PATENT DOCUMENTS

| WO | WO 9713513 A1 |   | 4/1997 |
|----|---------------|---|--------|
| WO | WO 98/30216   | * | 7/1998 |

OTHER PUBLICATIONS

Van der Glet et al., "A1158: AT1–Receptor Antagonists for Uremic Patients Using AN69 Dialysis Membranes", American Society of Nephrology, 31$^{st}$ Annual Meeting & Scientific Expostion, 1998.

Saracho et al., "Evaluation of the Losartan in Hemodialysis (ELHE) Study", 1998, Kioney International, vol. 54, No. 68;S–125 –S–129.

Zofia Wankowicz, "Cardiovascular agents in renal diseases", 1998, Med Sci Monit, vol. 4, No. 6;1104–1110.

* cited by examiner

*Primary Examiner*—Ray Henley
(74) *Attorney, Agent, or Firm*—Fish & Richardson PC

(57) ABSTRACT

The present invention relates to the use of an angiotensin II type 1 receptor antagonist in the manufacture of a medicament for the prophylactic and/or therapeutic treatment of cardiovascular complications encountered in a patient in need of dialysis. The invention further relates to a method for prophylactic and/or therapeutic treatment of cardiovascular complications encountered in a patient in need of dialysis, comprising administering to the patient a therapeutically effective amount of an angiotensin II type 1 receptor antagonist.

20 Claims, No Drawings

METHOD OF TREATMENT FOR CARDIOVASCULAR COMPLICATIONS

FIELD OF THE INVENTION

The present invention relates to the use of an angiotensin II type 1 receptor antagonist in the manufacture of a medicament for the prophylactic and/or therapeutic treatment of cardiovascular complications encountered in a patient in need of dialysis. The invention further relates to a method for prophylactic and/or therapeutic treatment of cardiovascular complications encountered in a patient in need of dialysis, comprising administering to the patient a therapeutically effective amount of an angiotensin II type 1 receptor antagonist.

BACKGROUND OF THE INVENTION

Compounds that interfere with the renin-angiotensin system (RAS) are well-known in the art and are used to treat cardiovascular diseases, particularly arterial hypertension and cardiac failure. Principally, the RAS can be interfered with by inhibition of the enzymes synthesizing angiotensins or by blocking receptors at the effector sites. Available today are renin-antagonists, inhibitors of the angiotensin converting enzyme (ACE) and angiotensin II (AT II) receptor antagonists.

Angiotensin II type 1 receptor antagonists for which the present invention has found a new medical use are thus known in the art. However, nothing has been disclosed in connection with their potential effects in dialysis and more particularly hemodialysis.

Hemodialysis is a process for removing waste products and toxins from the blood of patients with renal malfunction or failure. Blood is removed from, and returned to, circulation, either through an artificial arterio-venous fistula or a temporary or permanent internal catheter, and passes through an "artificial kidney", or dialyzer.

Dialyzers vary in design and performance, but all include a dialysis membrane and a dialys-ing solution. In dialysis, toxins are removed by diffusion through the dialysis membrane, thus essentially restoring blood to its normal state. The process, however, has to be repeated at regular intervals, e.g. two to three times per week for four to six hours per session.

Patients subject to hemodialysis are currently treated in hospitals, due to the high cost and the complexity of the dialysis equipment. For patients in hemodialysis, the prognosis has been improved over the last decades. One reason is improved dialysis equipment and procedures. Thus, new and more effective dialysis filters have been developed to allow more efficient dialysis with improved clearance of toxic substances. Another alternative to more effective dialysis filters is to use more frequent dialysis sessions. Currently, most patients are offered four hour dialysis sessions three times per week, all year round. Trials comparing frequency of dialysis sessions indicate that the survival rate will be improved if patients can accept such dialysis sessions four times per week. Understandably, all patients cannot manage such frequent hospital visits.

Mortality among patients treated with hemodialysis due to end-stage renal insufficiency is very high. A large proportion of these deaths, approximately 50 to 65%, are reported to be caused by cardiovascular complications. For example, in a Danish national registry report from 1996, cardiac causes of death and stroke were noted in 51% and 11% of the patients, respectively. Data from the European Registry, the so-called ERA-EDTA registry show that more than 44% of the hemodialyzed patients die of cardiac events, 33% of which from myocardial infarction and 23% from sudden death.

In most patients subject to hemodialysis, the non-functioning kidneys are left intact. The main reason for this, is that it involves major surgery to remove them.

It is likely that non-functioning kidneys excrete a number of kidney-derived toxic substances which increase the risk of cardiovascular complications in these patients.

Further support of this hypothesis, is that patients in hemodialysis who have had their kidneys removed seem to exhibit a reduced risk for such adverse effects on the cardiovascular system. Consequently, such patients run a reduced risk of cardiovascular complications.

Improved medical treatment of patients in hemodialysis has also resulted in prolonged survival as well as a reduced risk and duration of hospitalization due to complications. Although few large scale trials have been performed, treatment of cardiovascular diseases, such as hypertension, have improved. The infections which frequently occur in dialysis patients can nowadays be better managed. Furthermore, the restoration of red blood cell formation using e.g. recombinant erythropoetin (EPO) has improved the survival rate and increased quality of life (QoL).

Despite these medical advances, the prognosis for patients in dialysis, and especially chronic hemodialysis, remains poor. A medical treatment that can significantly reduce mortality and morbidity due to cardiovascular complications would clearly be a major therapeutic advance.

SUMMARY OF THE INVENTION

The inventors of the present invention, have surprisingly found that the cardiovascular complications, such as mortality and morbidity, encountered in patients subject to dialysis, especially chronic hemodialysis, due to end-stage renal disease can be reduced by using an angiotensin II type 1 receptor antagonist during and/or between the dialysis sessions. Thus, use of an angiotensin II type 1 receptor antagonist can significantly reduce mortality due to cardiovascular diseases and reduce the number and duration of hospitalizations due to cardiovascular complications.

The present invention thus relates to a new method of preventing and/or treating cardiovascular diseases and complications by pharmacological interference with the renin-angiotensin system (RAS) using an angiotensin II type 1 receptor antagonist.

Angiotensin II type 1 receptor antagonists are conventionally used for preventing and/or treating hypertension. The present invention, however, is directed to prevention and/or treatment of cardiovascular complications other than hypertension, e.g. mortality and morbidity as stated above. Further cardiovascular complications which may be prevented and/or treated with the present invention include, without limitation myocardial infarction (MI), stroke, vascular access dysfunction and amputations.

In one embodiment, the present invention relates to use of an angiotensin II type 1 receptor antagonist in the manufacture of a medicament for the prophylactic and/or therapeutic treatment of cardiovascular complications encountered during or between dialysis of a patient in need of such dialysis.

A further embodiment of the invention provides a method for prophylactic and/or therapeutic treatment of cardiovascular complications encountered in dialysis of a patient, comprising administering to a patient in need of such dialysis a therapeutically effective amount of an angiotensin II type 1 receptor antagonist.

DETAILED DESCRIPTION OF THE INVENTION

In preferred embodiments of the present invention use is made of an angiotensin II type 1 receptor antagonist of the general formula I:
wherein A is
or The compound of the general formula I wherein A is the I:1 moiety has the generic name losartan and is known from European Patent No. EP 0 253 310 B1 to du Pont.

The compound of the general formula I wherein A is the I:5 moiety has the generic name candesartan cilexetil and is known from European Patent No. 459 136 B1 and U.S. Pat. No. 5,196,444 to Takeda Chemical Industries.

The compound of the general formula I wherein A is the I:9 moiety has the generic name irbesartan.

The compound of the general formula I wherein A is the I:13 moiety has the generic name candesartan and is known from European Patent No. 459 136 B1 and U.S. Pat. No. 5,703,110 to Takeda Chemical Industries.

In preferred embodiments of the present invention, use is made of a compound of the general formula I wherein A I:5 (candesartan cilexetil) or A is I:13 (candesartan). Candesartan cilexetil is currently manufactured and sold worldwide e.g. under the trade names Atacand®, Amias® and Blopress®.

When the angiotensin II type 1 receptor antagonists used in the present invention have several asymetric carbon atoms, they can consequently exist in several stereochemical forms. The present invention includes the mixture of isomers as well as the individual stereoisomers. The present invention further includes geometrical isomers, rotational isomers, enantiomers, racemates and diastereomers.

Where applicable, the angiotensin II type 1 receptor antagonists may be used in neutral form, e.g. as a carboxylic acid, or in the form of a salt, preferably a pharmaceutically acceptable salt such as the sodium, potassium, ammonium, calcium or magnesium salt of the compound at issue. Where applicable the compounds listed above can be used in hydrolyzable ester form.

In the present invention, angiotensin II type 1 receptor antagonists include all prodrugs thereof, whether active or inactive in vitro. Thus, although such protected derivatives may not possess pharmacological activity per se, they may be administered e.g. parenterally or orally, and thereafter metabolized in vivo to form pharmacologically active angiotensin II type 1 receptor antagonists.

The angiotensin II type 1 receptor antagonists may be used prior to and/or during dialysis.

In the present invention, dialysis includes hemodialysis and peritoneal dialysis. The present invention is preferably used for treating patients in hemodialysis, especially in chronic hemodialysis.

In the present invention, treatment of patients "in need of (treatment by) dialysis" relates to prophylactic and/or therapeutic treatment of patients suffering from renal complications and/or renal failure, including chronic and/or acute renal failure. The term also includes the prophylactic and/or therapeutic treatment of patients with intoxication by compounds that may give rise to organ damage, severe metabolic disturbances and/or death.

The present invention also relates to use of an angiotensin II type 1 receptor antagonist in the manufacture of a medicament for the prophylactic and/or therapeutic treatment of cardiovascular complications encountered in dialysis of a patient in need of such dialysis, wherein the angiotensin II type 1 receptor antagonist is provided in the dialysing solution.

The angiotensin II type 1 receptor antagonists may be provided as part of a dialysing solution ready for use in dialysis or provided as part of a dialysis concentrate, which concentrate is to be diluted before being used as part of a dialysing solution.

Normally, however, the angiotensin II type 1 receptor antagonists are administered by the oral or parenteral route, e.g. by intravenous, subcutaneous or intramuscular administration. Other possible routes of administration include rectal and transdermal administration. The formulation may be given in dosage unit form, especially as tablets or capsules.

According to a further aspect of the invention, there is provided a pharmaceutical formulation for use in the prophylactic and/or therapeutic treatment of cardiovascular complications encountered in dialysis of a patient in need of such dialysis, comprising an angiotensin II type 1 receptor antagonist as active substance in optional admixture with pharmaceutically acceptable adjuvants, diluents and/or carriers.

The adjuvants, diluents and/or carriers used in the pharmaceutical formulations of the present invention, may be conventional ones well known to the person skilled in the art. Examples of such adjuvants, diluents and/or carriers include substances used as binders, lubricants, fillers, disintegrants, pH regulants and thickeners as well as substances included for providing isotonic solutions.

The dose of the angiotensin II type 1 receptor antagonist and in particular a compound according to formula I to be administered in prophylaxis and/or treatment of dialysis patients will depend primarily upon the angiotensin II type 1 receptor antagonists which is used, the route of administration, the severity of the disease to be treated and the status of the patient. The daily dose, especially at oral, rectal as well as parenteral administration, can be in the range of from about 0.01 mg to about 1000 mg per day of active substance, suitably from 0.1 mg to 500 mg per day of active substance, particularly from 1 mg to 100 mg per day of active substance. In preferred embodiments where candesartan and derivatives thereof are used, including candesartan cilexetil, the dosage range at oral, rectal as well as parenteral administration can be in the range of from about 0.1 mg to about 50 mg per day, particularly from 0.2 mg to 25 mg per day calculated as candesartan.

EXAMPLE

The invention is illustrated by reference to the following Example which is not intended to limit the invention in any way.

Example 1

Pilot Study Design

A pilot study in which the effects of the angiotensin II type 1 receptor antagonist candesartan cilexetil (Atacand®) is compared to that of placebo, will be carried out to explore the feasability of giving candesartan cilexetil to patients in need of hemodialysis to reduce cardiovascular complications.

The pilot study will be double-blind placebo controlled performed in patients receiving hemodilaysis. The persons will be 2:1 randomized to treatment with active or inactive medication, such that 14 persons will receive candesartan cilexetil (Atacand®) and 7 persons will receive placebo. The dose titration will be 4 to 8 to 16 based on tolerance, two weeks allowed per dose.

The study will provide preliminary data on the feasibility of administering candesartan cilexetil to hemodialysis patients. It may also provide preliminary data on useful concentrations of candesartan cilexetil.

Example 2
Large-scale Study Design

A large-scale clinical trial in which the effects of the angiotensin II type 1 receptor antagonist candesartan cilexetil (Atacand®) is compared to that of placebo, will be carried out to explore the usefulness of giving candesartan cilexetil to patients in need of hemo-dialysis to reduce cardiovascular complications.

Treatments will be given to patients undergoing chronic hemodialysis treatment due to renal insufficiency. Patients will be recruited from hospitals with special dialysis departments. The patients will be randomized to double-blind treatment with active or inactive medication, i.e. candesartan cilexetil or placebo.

The study will also provide more detailed data on the feasibility of administering candesartan cilexetil to hemodialysis patients. It may also provide data on useful concentrations of candesartan cilexetil.

What is claimed is:

1. A method for preventive treatment of cardiovascular complications encountered in a patient in need of dialysis, comprising administering to such a patient a therapeutically effective amount of an angiotensin II type 1 receptor antagonist.

2. The method according claim 1, wherein the angiotensin II type 1 receptor antagonist is administered by the oral or parenteral route.

3. The method according to claim 1, wherein the angiotensin II type 1 receptor antagonist is administered by the rectal or transdermal route.

4. The method according to claim 1, wherein the angiotensin II type 1 receptor antagonist is administered in dosage unit form, suitably as tablets or capsules.

5. The method according to claim 1, wherein the angiotensin II type 1 receptor antagonist is provided in the dialysing solution.

6. The method according to claim 1, wherein the dialysis is hemodialysis.

7. The method according to claim 1, wherein the cardiovascular complication is selected from the group consisting of mortality and morbidity.

8. The method according to claim 1, wherein the cardiovascular complication is selected from the group consisting of myocardial infarction (MI), stroke, vascular access dysfunction and amputations.

9. The method according to claim 1, wherein the angiotensin II type 1 receptor antagonist is a compound of the general formula I
wherein A is selected from the group consisting of
and
or pharmaceutically acceptable salts and stereochemical isomers of any of these.

10. The method according to claim 9, wherein the angiotensin II type 1 receptor antagonist is a compound of the general formula I wherein A is I:5 or I:13.

11. A method for therapeutic treatment of cardiovascular complications encountered in a patient in need of dialysis, comprising administering to such a patient a therapeutically effective amount of an angiotensin II type 1 receptor antagonist.

12. The method according to claim 11, wherein the angiotensin II type 1 receptor antagonist is administered by the oral or parenteral route.

13. The method according to claim 11, wherein the angiotensin II type 1 receptor antagonist is administered by the rectal or transdermal route.

14. The method according to claim 11, wherein the angiotensin II type 1 receptor antagonist is administered in dosage unit form, suitably as tablets or capsules.

15. The method according to claim 11, wherein the angiotensin II type 1 receptor antagonist is provided in the dialysing solution.

16. The method according to claim 11, wherein the dialysis is hemodialysis.

17. The method according to claim 11, wherein the cardiovascular complication is selected from the group consisting of mortality and morbidity.

18. The method according to claim 11, wherein the cardiovascular complication is selected from the group consisting of myocardial infarction (MI), stroke, vascular access dysfunction and amputations.

19. The method according to claim 11, wherein the angiotensin II type 1 receptor antagonist is a compound of the general formula I
wherein A is selected from the group consisting of
and
or pharmaceutically acceptable salts and stereochemical isomers of any of these.

20. The method according to claim 19, wherein the angiotensin II type 1 receptor antagonist is a compound of the general formula I wherein A is I:5 or I:13.

* * * * *

UNITED STATES PATENT AND TRADEMARK OFFICE
CERTIFICATE OF CORRECTION

PATENT NO. : 6,486,188 B1
DATED : November 26, 2002
INVENTOR(S) : Erling Bjerregaard-Pedersen et al.

It is certified that error appears in the above-identified patent and that said Letters Patent is hereby corrected as shown below:

<u>Title page,</u>
Item [75], Inventors, please replace "Faies Zannad" with -- Faiez Zannad --.

Signed and Sealed this

Eleventh Day of May, 2004

JON W. DUDAS
*Acting Director of the United States Patent and Trademark Office*